United States Patent
Aoki et al.

(10) Patent No.: US 6,764,827 B1
(45) Date of Patent: Jul. 20, 2004

(54) ANTI-HUMAN MEDULLASIN MONOCLONAL ANTIBODY PROCESS FOR PRODUCING THE SAME AND IMMUNOASSAY USING THE SAME

(75) Inventors: Yosuke Aoki, Hino (JP); Hideaki Suzuki, Tokyo (JP); Kiyoshi Takahashi, Tokyo (JP); Hisashi Katsuragi, Tokyo (JP)

(73) Assignee: Dainichiseika Color & Chemicals MFG. Co., Ltd., Tokyo (JP)

( * ) Notice: Subject to any disclaimer, the term of this patent is extended or adjusted under 35 U.S.C. 154(b) by 0 days.

(21) Appl. No.: 09/384,379

(22) Filed: Aug. 27, 1999

(51) Int. Cl.⁷ ............................................. G01N 33/543
(52) U.S. Cl. ..................... 435/7.92; 435/7.1; 435/7.94; 436/518; 436/547; 436/548; 530/386; 530/387.1; 530/388.1; 530/388.15; 530/861
(58) Field of Search ................................ 435/7.1, 7.92, 435/7.94; 436/518, 547, 548; 530/386, 387.1, 388.1, 388.15, 861

(56) References Cited

U.S. PATENT DOCUMENTS 5,661,000 A * 8/1997 Aoki et al.

FOREIGN PATENT DOCUMENTS

| JP | A11151085 | 6/1999 |
| JP | 11151085 A * | 6/1999 |

OTHER PUBLICATIONS

Aoki et al., Clinica Chimica Acta. 178: 193–201. 1988.*
Kohler, Georges. Science. 233:1281–1286. 1996.*

* cited by examiner

*Primary Examiner*—Bao-Thuy L. Nguyen
(74) *Attorney, Agent, or Firm*—Birch, Stewart, Kolasch & Birch, LLP

(57) ABSTRACT

A monoclonal antibody by which medullasin that is a kind of serine proteases existing in granulocytes, production process thereof and an immunoassay of human medullasin using the antibody are disclosed. The monoclonal antibody specifically recognizes human medullasin. The process for producing the anti-human medullasin antibody comprises culturing hybridomas prepared by cell fusion between antibody-producing cells recovered from an animal immunized with human medullasin and myeloma cells, and recovering anti-human medullasin monoclonal antibody which specifically recognizes human medullasin from the culture in which the hybridomas are cultured. The immunoassay utilizes the anti-human medullasin antibody.

5 Claims, 1 Drawing Sheet

ANTI-HUMAN MEDULLASIN MONOCLONAL ANTIBODY PROCESS FOR PRODUCING THE SAME AND IMMUNOASSAY USING THE SAME

BACKGROUND OF THE INVENTION

1. Field of the Invention

The present invention relates to an anti-human medullasin monoclonal antibody, process for producing the same and immunoassay using the same.

2. Description of the Related Art

Medullasin which is a kind of serine proteases occurs in granulocytes and the like, and is thought to widely play important roles in defense mechanism, including expression of inflammation, especially chronic inflammation. The amount of medullasin in granulocytes is increased in advanced stage of a number of chronic inflammatory diseases, and is normalized in remission stage. It is observed in patients suffering from multiple sclerosis that the amount of medullasin is prominently increased several days before the advanced stage and is normalized before remission. Multiple sclerosis is an intractable chronic inflammatory disease which mostly results in death in 10 to 15 years, which is characterized by localized demyelinated lesion in white matter of central nerve system and gliosis, and progresses repeating remission and aggravation. Although the cause of this disease has not been clarified, it is thought that this disease is a kind of autoimmune diseases in which autoantibodies attack the nerve tissue upon stimulation of the immune system by a virus or a bacterium. Its diagnosis is quite difficult and is now carried out by nuclear magnetic resonance imaging (MRI) or the like. However, MRI or the like requires a very large-scale equipment and high skill in the measuring operation, and is costly. Thus, a simple diagnosis method by which diagnosis of the disease, understanding of the state of the disease and assumption of the consequence can be accomplished is now being developed. For this, methods for measuring the activity of medullasin in granulocytes in the blood are now studied, and a method based on the ability of medullasin to inactivate apo-ornithine transaminase has been developed. However, since measurement of the activity of medullasin in granulocytes by an enzymatic chemical method is very complicated, simple immunoassay was tried and has been developed, which utilizes a polyclonal antibody.

However, the immunoassay for measuring human medullasin using a polyclonal antibody has drawbacks in that the reactivity of the antibody is not necessarily sufficient, the measuring time is long and the measuring operation is somewhat complicated. Thus, an immunoassay utilizing a monoclonal antibody, by which human medullasin can be measured quickly and simply, is demanded.

SUMMARY OF THE INVENTION

The present invention was accomplished under these circumstances and an object of the present invention is to provide a monoclonal antibody which specifically recognizes human medullasin and a method for specifically measuring human medullasin quickly and simply.

The present inventors intensively studied to attain the above-mentioned object and succeeded in obtaining an anti-human medullasin monoclonal antibody by culturing hybridomas prepared by cell fusion between antibody-producing cells recovered from an animal immunized with human medullasin separated and purified from human granulocytes and myeloma cells according to the method by Köhler and Milstein, and discovered that human medullasin can be measured specifically, quickly and simply by using this antibody, thereby reaching the present invention.

According to the first aspect, the present invention provides an anti-human medullasin monoclonal antibody which specifically recognizes human medullasin.

According to the second aspect, the present invention provides a process for producing an anti-human medullasin monoclonal antibody comprising culturing hybridomas prepared by cell fusion between antibody-producing cells recovered from an animal immunized with human medullasin and myeloma cells, and recovering anti-human medullasin monoclonal antibody which specifically recognizes human medullasin from the culture in which the hybridomas are cultured.

According to the third aspect, the present invention provides an immunoassay comprising immobilizing human medullasin in a test sample by sandwiching the human medullasin between an anti-human medullasin monoclonal antibody immobilized on an insoluble carrier and a labelled anti-human medullasin monoclonal antibody by antigen-antibody reactions to form a complex, and quantifying the label in the complex.

By the present invention, an anti-human medullasin monoclonal antibody which specifically recognizes medullasin that is a kind of serine proteases existing in granulocytes was provided. By utilizing this monoclonal antibody, quick and simple immunoassay for measuring human medullasin was provided, which may be used for hemodiagnosis or the like for chronic inflammatory diseases, especially multiple sclerosis.

DETAILED DESCRIPTION OF THE PREFERRED EMBODIMENTS

Figure 1:
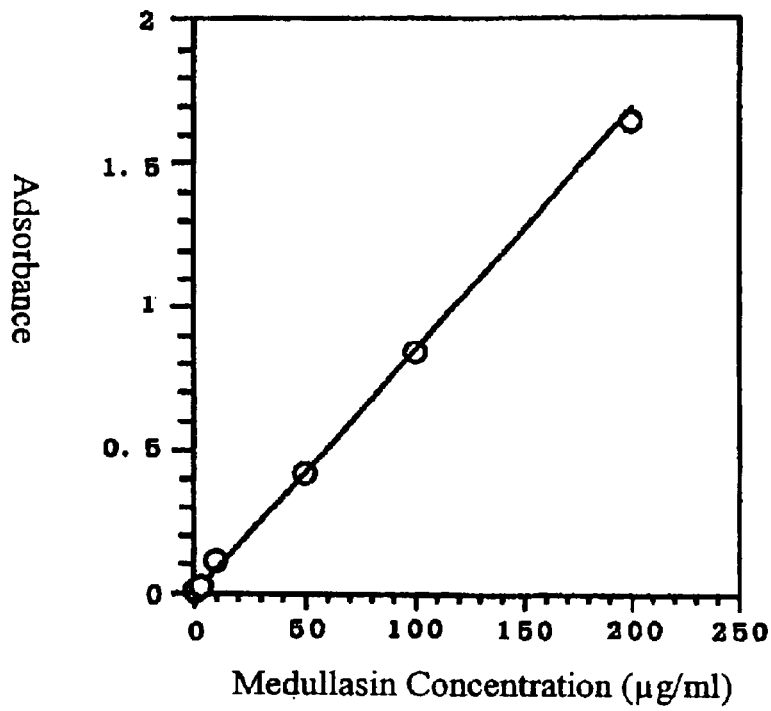
FIG. 1 is a calibration curve for measuring human medullasin, prepared by plotting the absorbance measured by the enzyme immunoassay (Measuring Method I) described in Example 2 as a function of the concentration of the antigen.

The anti-human medullasin monoclonal antibody according to the present invention may be produced by culturing hybridomas in a culture medium, which hybridomas were prepared by cell fusion between antibody-producing cells recovered from an animal immunized with human medullasin extracted from granulocytes separated from the blood of a normal individual and myeloma cells, and recovering the monoclonal antibody from the culture, or by intraperitoneally administering the hybridomas to an animal, proliferating the hybridomas in ascites, and recovering the monoclonal antibody from the ascites.

Hybridomas which secrete anti-human medullasin monoclonal antibodies designated as 3F03 and 2E04 have been deposited on the 30th day of January, 2004 at the International Patent Organism Depository, National Institute of Advanced Industrial Science and Technology, which is located at Tsukuba Central 6, 1—1, Higashi 1-chome, Tsukuba-shi, Ibaraki-ken, Japan. The deposits were assigned accession numbers FERM BP-08606(3F03) and FERM BP-08605(2E04). The above depository will be permanent and readily accessible thereto by the public if a patent is granted, under conditions which assure (a) that access to the culture will be available during pendency of said patent application to one determined by the Commissioner to be entitled thereto under. 37 C.F.R. 1.14 and 35 U.S.C. 122, and (b) that all restrictions on the availability to the public of the above-mentioned culture will be irrevocably removed upon the granting of a patent. In the event that any of the strains should become non-viable, mutate or inadvertently destroyed, the deposit will be replaced at the above-mentioned depository. The above-mentioned deposit will be maintained (1) for thirty (30) years from the date of deposit, (2) for five (5) years after the last request for the deposit at the depository which is made during the enforceable life of any patent which will issue from the above-identified application or (3) for the enforceable life of any patent which issues from the present application, whichever is longer.

The hybridomas producing the anti-human medullasin monoclonal antibody according to: the present invention may be produced by the so called cell fusion method. That is, the desired monoclonal antibody-producing hybridoma may be obtained by recovering antibody-producing cells from an animal immunized with human medullasin, fusing the antibody-producing cells with myeloma cells, selectively proliferating the obtained hybridomas, screening the antibody-producing hybridomas from the obtained hybridomas, and cloning the selected hybridomas.

Examples of the antibody-producing cells include spleen cells, lymph node cells, B lymphocytes and the like, which are obtained from an animal immunized with human medullasin or a composition or cells containing human medullasin. Examples of the animal to be immunized include mouse, rat, rabbit, goat, sheep, horse and the like. Immunization may be carried out by, for example, subcutaneously, intramuscularly or intraperitoneally administering human medullasin to an animal with a dose of about 1 μg to 1 mg/time, once or twice per month for 1 to 6 months. Collection of the antibody-producing cells may be carried out 2 to 4 days after the final immunization.

The myeloma cells may be originated from mouse, rat or the like. The antibody-producing cells and the myeloma cells may preferably be originated from the same animal species.

The method of cell fusion may be arbitrarily selected. For example, cell fusion may be carried out by mixing the antibody-producing cells and the myelomna cells in a medium such as Dulbecco's Modified Eagle Medium (DMEM) in the presence of a fusion accelerator such as polyethylene glycol.

After the cell fusion operation, the hybridomas may be selected by appropriately diluting the cells after cell fusion operation with DMEM or the like, centrifuging the resultant, suspending the precipitate in a selection medium such as HAT medium, and culturing the cells therein. Antibody-producing hybridomas are then screened by enzyme immunoassay or the like using the culture supernatant, and the selected hybridoma is cloned by limiting dilution method to obtain the hybridoma producing the anti-human medullasin monoclonal antibody according to the present invention.

The monoclonal antibody according to the present invention may be produced by culturing the thus obtained antibody-producing hybridoma in an appropriate culture medium or in an animal, and recovering the monoclonal antibody from the culture. To produce a large amount of monoclonal antibody, the method in which the hybridomas are intraperitoneally administered to an animal of the same species as the donor of the myeloma cells, the monoclonal antibody according to the present invention is accumulated in the ascites, and the monoclonal antibody is recovered from the ascites, is preferred. Before the intraperitoneal administration of the antibody-producing hybridomas, it is preferred to administer a mineral oil such as pristane.

The monoclonal antibody according to the present invention may be separated from the culture or ascites by fractionation with ammonium sulfate, anion-exchange column chromatography or column chromatography using protein A, G or the like, which is usually employed for purification of IgG.

Four kinds of anti-human medullasin monoclonal antibodies according to the present invention, designated 3F03, 3G03, 2E04 and 1G12, have been obtained. All of these monoclonal antibodies belong to immunoglobulin class IgG, subclass $IgG_1$, and specifically react with human medullasin which is the corresponding antigen.

Therefore, by using the anti-human medullasin monoclonal antibody according to the present invention, human medullasin may be immunologically measured. The immunoassay for measuring human medullasin using the monoclonal antibody according to the present invention may be arbitrarily selected. A competition method in which the antigen in a sample is reacted with the monoclonal antibody immobilized on an insoluble carrier in the presence of a labeled antigen; and a sandwich method in which the antigen in a sample is reacted with the monoclonal antibody immobilized on an insoluble carrier, and then the monoclonal antibody which is labeled is reacted with the resultant to form an antibody-antigen-antibody sandwich complex, are preferred. In the enzyme immunoassay according to the sandwich method, it is required that the corresponding epitopes of the immobilized antibody and of the labeled antibody be different, so that monoclonal antibodies of which corresponding epitopes are different are used in combination for constituting the immunoassay system. However, immunoassay system was successfully prepared by using the monoclonal antibody 2E04 according to the present invention as both the immobilized antibody and as the labeled antibody. This is because human medullasin has epitopes in a single molecule, whose amino acid sequences are identical. Examples of the insoluble carriers used for these measuring methods include beads made of a plastic such as polystyrene, and microplate. Preferred examples of the label used for labeling the antibody include enzymes, fluorescent substances, luminescent substances and radioactive substances. Examples of the enzymes include peroxidase, alkaline phosphatase, β-D-galactosidase and the like. Examples of the fluorescent substances include fluorescein isocyanate, phycobiliprotein and the like. Examples of the luminescent substances include luminols, dioxetanes, acridinium salts and the like. Examples of the radioactive substances include $^{125}I$, $^{131}I$, $^{111}In$, $^{99m}Tc$ and the like. In cases where the labeling substance is an enzyme, a substrate, and if necessary, a coloring agent, scintillator, luminescent agent or the like are used. In cases where peroxidase is used as the enzyme, hydrogen peroxide or the like may be used as the substrate, 2,2'-azinodi[3-ethylbenzthiazoline sulfonic acid] ammonium salt (ABTS), 5-aminosalicylic acid, o-phenylenediamine, 4-aminoantipyrine, 3,3',5,5'-tetramethylbenzidine or the like may be used as the coloring agent, 4-hydroxyphenylacetic acid, 3-(4-hydroxyphenyl) propionic acid or the like may be used as the scintillator, and luminols or the like may be used as the luminescent agent. In cases where alkaline phosphatase is used as the enzyme, 4-nitrophenylphosphate, 4-methylumbelliferyl phosphate, cortisol-21-phosphate or the like may be used as the substrate. In cases where β-D-galactosidase is used as the enzyme, 2-nitrophenyl-β-D-galactoside, 3-(2'spiroadamantane)-4-methoxy-4(3"-β-D-galactosyloxyphenyl)-1,2-dioxetane (AMPGD) or the like may be used as the substrate.

EXAMPLES

The present invention will now be described more concretely by way of reference examples and examples. However, the present invention is not restricted to the examples.

In all examples, all % are by weight.

Reference Example 1

Four hundred milliliters of the blood from a normal individual and 6% dextran (molecular weight: 200,000–300,000) solution in physiological saline were mixed at a ratio of blood:aqueous dextran solution=2:1, and the resulting mixture was lightly stirred with a glass rod, followed by leaving to stand the resultant at 4–8° C. for about 1 hour. The precipitated red blood cells were removed and the obtained supernatant was centrifuged at 15,000 rpm, followed by recovering the precipitate to obtain leukocytes. To the obtained leukocytes, extraction buffer containing 1 mM ethylenediamine tetraacetic acid disodium salt (EDTA) and 1 mM p-chloromercury benzoic acid (PCMB) in 1 M potassium phosphate buffer (PKB) (pH 7.0) was added and the resulting mixture was incubated under stirring at 37° C. for 20 minutes. The resultant was subjected to ultrasonication for 15 seconds to completely disrupt the cells and the resultant was incubated at 37° C. for 20 minutes, followed by centrifugation at 4° C. at 12,000 rpm for 10 seconds. The supernatant was recovered and dialyzed against distilled water. The precipitated residue was subjected to the above-described operations several times to carry out extraction. The obtained extracted fluid was applied to a CM-Sepharose gel column equilibrated with 50 mM PKB (pH 6.0) and the column was washed with the same buffer. The adsorbed substances were then eluted with 1 M PKB (pH 6.0) and the eluted solution was dialyzed against distilled water overnight to remove salt, followed by concentrating the resultant with a collodion membrane, to obtain 1.5 mg of purified human medullasin.

Example 1

Preparation of Anti-human Medullasin Monoclonal Antibody (1) Preparation of Hybridomas by Cell Fusion between Antibody-producing Cells and Myeloma Cells The human medullasin extracted and purified from human granulocytes was emulsified with Freund's complete adjuvant and the resultant was subcutaneously administered to a BALB/c mice of 7 weeks old at a dose of 50 μg/mouse. Four weeks later, the mice were subjected to additional immunization by the same method as the first immunization. Seven days after the additional immunization, increase in the blood level of antibodies was confirmed. Another 7 days later, the antigen was intraperitoneally administered at a dose of 50 μg/mouse as the final immunization. On the other hand, mouse myeloma P3-X63-Ag8-U1(P3U1) cells were passaged in DMEM supplemented with 20% fetus calf serum.

Three days after the final immunization, spleen cells were collected from the mice and fused with P3U1 cells using polyethylene glycol 4000. After the cell fusion operation, the medium was changed to DMEM supplemented with 100 μM hypoxanthine, 0.4 μM aminopterin and 16 μM thymidine (HAT medium), and the resultant was placed in wells of a 96-well microplate. By continuing the selective culture for 2 to 3 weeks, hybridomas between the spleen cells and the myeloma cells were obtained.

(2) Screening of Anti-human Medullasin Antibody-producing Hybridomas

The titers of the antibodies in the culture fluids of the hybridomas were determined by ELISA (enzyme-linked immunosorbent assay), thereby carrying out screening. That is, human medullasin was adsorbed on the wells of a microplate for ELISA, and the wells were blocked with 1% bovine serum albumin (BSA) solution in 10 mM phosphate-buffered saline (PBS) (pH 7.4). Fifty microliters of the hybridoma culture was added to each well and the resultant was left to stand for 1 hour. After removing the hybridoma culture and washing the wells, 100 μl of 2 μg/ml solution of peroxidase-labeled goat anti-mouse IgG Fc antibody in PBS was added to each well, and the resulting mixture was allowed to react at 37° C. for 1 hour. After removing the enzyme-labeled antibody solution and washing the wells, 200 μl of 0.1M phosphate citrate buffer (pH 4.6) containing 0.05% ABTS and 0.0034% hydrogen peroxide was added to each well to generate color, thereby selecting the anti-human medullasin antibody-producing hybridomas.

(3) Cloning of Antibody-Producing Cells and Preparation of Monoclonal Antibodies Each of the cultures of the anti-human medullasin antibody-producing hybridomas was subjected to cloning by the limiting dilution method to finally obtain 4 kinds of monoclonal hybridoma. The hybridomas were separately administered to BALB/c mice intraperitoneally which mice preliminarily received pristane and the hybridomas were grown to obtain ascites each containing the monoclonal antibody. To the obtained ascites, 50% saturated ammonium sulfate was added to precipitate the antibody and the antibody was dissolved in PBS. The resulting solution was dialyzed against 50 mM Tris-HCl buffer (pH 7.8) containing 3 M NaCl and the resultant was applied to a Protein A-Sepharose CL4B Column (commercially available from Pharmacia). The adsorbed antibody was eluted with 0.1 M glycine-HCl buffer (pH 6.0) and the eluted solution was neutralized, followed by purification of antibody therefrom to obtain 4 kinds of monoclonal antibody, 3F03, 3G03, 2E04 and 1G12.

(4) Properties of Monoclonal Antibodies Western Blotting

The antigen corresponding to the monoclonal antibodies was immobilized by Western blotting method.

First, medullasin from human granulocytes was subjected to SDS-polyacrylamide gel electrophoresis according to the method by Laemmli. The protein was transferred from the slab gel to a nitrocellulose sheet using an electrolyte buffer containing 25 mM Tris-(hydroxymethyl)aminomethane, 192 mM glycine and 20% methanol, at a voltage slope of 7 V/cm for 2 hours. Each lane on the nitrocellulose sheet was cut and one of the sheets was subjected to protein staining with Amideblack and the other sheet was subjected to enzyme immunoassay as follows. That is, after blocking the sheet with 1% BSA/PBS, the mouse anti-human medullasin monoclonal antibody was added as a primary antibody, and then alkaline phosphatase-labeled goat anti-mouse IgG Fc antibody was added as a secondary antibody, and the resultant was allowed to react. After washing the sheet, a substrate solution containing 5-bromo-4-chloro-3-indolylphosphate (0.7×10³M)/Nitroblue tetrazolium salt (0.7×10³M) in 0.1M Tris-HCl buffer (pH 9.5) was added to generate color. By this, it was confirmed that all of the 4 mouse anti-human medullasin monoclonal antibodies recognize medullasin from human granulocytes.

Inhibition Assay

Human medullasin immobilized on the wells of a microplate for ELISA was reacted with a biotinylated first antibody in the presence of a non-labeled second antibody, and then avidin-conjugated peroxidase was reacted, followed by addition of a substrate solution to generate color, thereby carrying out inhibition assay. By this, with any combination of the monoclonal antibodies, the amount of the reacted biotinylated antibody was not changed. Therefore, it was confirmed that the 4 monoclonal antibodies recognize epitopes which are different each other.

Example 2

Immunoassay I of Human Medullasin (1) Preparation of Beads on which Monoclonal Antibody is Immobilized After well washing polystyrene beads (6 mm diameter), the beads were immersed in 10 μg/ml solution of mouse anti-human medullasin monoclonal antibody (2E04) in PBS (pH 7.4) at 4° C. for one day and the beads were washed with PBS, followed by blocking the beads with aqueous 1% BSA solution at 4° C. for one day to obtain beads on which the monoclonal antibody was immobilized.

(2) Preparation of Peroxidase-labeled Monoclonal Antibody

To 1.0 mg/ml solution of mouse anti-human medullasin monoclonal antibody (2E04) in PBS, 0.1 ml of 10 mg/ml solution of N-(m-maleimide benzoic acid)-N-succinimide ester (MBS) in dimethylformamide was added and the mixture was allowed to react at 25° C. for 30 minutes. The reaction mixture was applied to a Sephadex G-25 column and gel permeation chromatography was carried out using 0.1 M phosphate buffer pH 6.0) to separate maleimide-bound monoclonal antibody and the non-reacted MBS.

On the other hand, to 1.0 mg/ml horse radish peroxidase (HRP) solution as an enzyme in PBS, 10 mg/ml solution of N-succinimidyl-3-(2-pyridylthio)propionate (SPDP) in ethanol was added and the mixture was allowed to react at 25° C. for 30 minutes. The reaction mixture was applied to a Sephadex G-25 column and subjected to gel permeation with 10 mM acetate buffer (pH 4.5). The fractions containing pyridyl disulfide-bound HRP were collected and were about 10-fold concentrated in a collodion bag in ice. To the resultant, 1 ml of 0.1 M acetate-buffered physiological saline (pH 4.5) containing 0.1 M dithiothreitol was added and the resulting mixture was stirred at 25° C. for 30 minutes to reduce the pyridyl disulfide group introduced into the HRP molecule, followed by gel permeation chromatography of the resulting mixture using Sephadex G-25 to obtain a fraction containing thiol-bound HRP.

Then the maleimide-bound monoclonal antibody and the thiol-bound HRP were mixed and the mixture was concentrated to a protein concentration of 4 mg/ml in a collodion bag in ice. After leaving the resultant to stand at 4° C. for one day, the resultant was subjected to gel permeation chromatography using Ultrogel AcA44 (commercially available from SEPRACOR) to obtain a peroxidase-labeled monoclonal antibody.

(3) Sandwich Enzyme Immunoassay of Human Medullasin

In a test tube, one bead on which the mouse anti-human medullasin monoclonal antibody (2E04) was immobilized, 50 μl of 2% BSA-containing PBS solution containing purified human medullasin (standard substance) in a concentration of 0, 1, 10, 100 or 200 ng/ml, and 350 μl of 2% BSA-containing PBS solution containing 0.2 μg/ml HRP-labeled mouse anti-human medullasin monoclonal antibody (2E04) were placed and the mixture was incubated at 37° C. for 30 minutes. After removing the contents of the test tube by aspiration, the test tube was washed with physiological saline and 400 μl of 0.1 M phosphate citrate buffer (pH 4.6) containing 0.05% ABTS and 0.0034% hydrogen peroxide was added to each test tube. After incubating the mixture at 37° C. for 30 minutes, 1 ml of 0.1N aqueous oxalic acid solution was added to each test tube to stop the enzyme reaction and the absorbance at 420 nm of the resulting solution was measured with a spectrophotometer. By plotting the measured absorbance with respect to the concentration of the standard substance, a calibration curve with good concentration dependence as shown in FIG. 1 was obtained using the same monoclonal antibody as the immobilized antibody and as the enzyme-labeled antibody.

Example 3

Immunoassay II of Human Medullasin (1) Preparation of Beads on which Monoclonal Antibody is Immobilized After well washing polystyrene beads (6 mm diameter), the beads were immersed in 10 μg/ml solution of mouse anti-human medullasin monoclonal antibody (3F03) in PBS (pH 7.4) at 4° C. for one day and the beads were washed with PBS, followed by blocking the beads with aqueous 1% BSA solution at 4° C. for one day to obtain beads on which the monoclonal antibody was immobilized.

(2) Sandwich Enzyme Immunoassay of Human Medullasin

Figure 2:
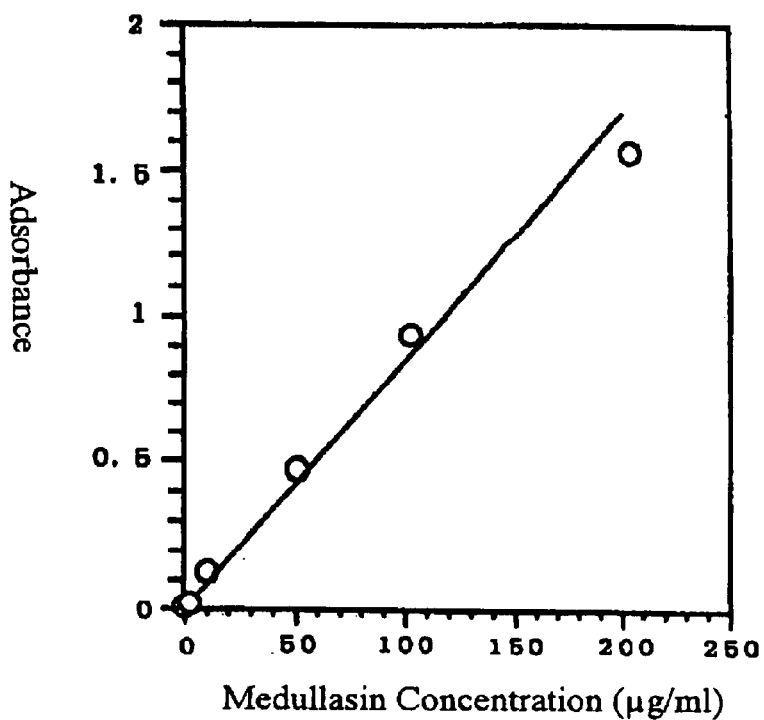
FIG. 2 is a calibration curve for measuring human medullasin, prepared by plotting the absorbance measured by the enzyme immunoassay (Measuring Method II) described in Example 3 as a function of the concentration of the antigen.

In a test tube, one bead on which the mouse anti-human medullasin monoclonal antibody (3F03) was immobilized, 50 μl of 2% BSA-containing PBS solution containing purified human medullasin (standard substance) in a concentration of 0, 1, 10, 100 or 200 ng/ml, and 350 μl of 2% BSA-containing PBS solution containing 0.2 μg/ml HRP-labeled mouse anti-human medullasin monoclonal antibody (2E04) were placed and the mixture was incubated at 37° C. for 30 minutes. After removing the contents of the test tube by aspiration, the test tube was washed with physiological saline and 400 μl of 0.1 M phosphate citrate buffer (pH 4.6) containing 0.05% ABTS and 0.0034% hydrogen peroxide was added to each test tube. After incubating the mixture at 37° C. for 30 minutes, 1 ml of 0.1N aqueous oxalic acid solution was added to each test tube to stop the enzyme reaction and the absorbance at 420 nm of the resulting solution was measured. By plotting the measured absorbance with respect to the concentration of the standard substance, a calibration curve with good concentration dependence as shown in FIG. 2 was obtained.

Example 4

Measurement of Medullasin in Clinical Samples by Enzyme Immunoassay

Samples of frozen blood collected from a normal individual and from a patient suffering from multiple sclerosis were thawed at room temperature and 10 μl of each sample was added to 2 ml of PBS (pH 7.4), followed by uniformly mixing the mixture to prepare sample solutions. To a test tube, 10 μl of each sample solution was added and 40 μl of 2.5% BSA-containing PBS (pH 7.4) was added to dilute the sample solution. To the test tube, one bead on which the mouse anti-human medullasin monoclonal antibody 2E04 or 3F03 was immobilized and 350 µl of 2% BSA-containing PBS solution containing 0.2 µg/ml HRP-labeled mouse anti-human medullasin monoclonal antibody (2E04) were added and the resulting mixture was incubated at 37° C. for 30 minutes. In exactly the same manner as in the above-described preparation of the calibration curves, washing, enzyme reaction, stopping of the reaction and measurement of absorbance at 420 nm with a spectrophotometer were carried out, and the concentration of human medullasin was determined based